United States Patent [19]

Noda et al.

[11] Patent Number: 5,519,046

[45] Date of Patent: May 21, 1996

[54] KETOROLAC-CONTAINING FOMENTATION

[75] Inventors: Kanji Noda; Masaru Saita; Munehiko Hirano; Yasuhiro Ikeura; Yasuaki Taniguchi; Terushi Hashiguchi; Yasuhisa Kose; Yasunori Takada; Eiji Kyoya; Akira Nakagawa, all of Tosu, Japan

[73] Assignee: Hisamitsu Pharmaceutical Co., Inc., Tosu, Japan

[21] Appl. No.: 232,287

[22] PCT Filed: Nov. 6, 1992

[86] PCT No.: PCT/JP92/01446

§ 371 Date: May 6, 1994

§ 102(e) Date: May 6, 1994

[87] PCT Pub. No.: WO93/09768

PCT Pub. Date: May 27, 1993

[30] Foreign Application Priority Data

Nov. 11, 1991 [JP] Japan ................................. 3-323647

[51] Int. Cl.$^6$ ................................................. A61K 31/40
[52] U.S. Cl. ............................................................. 514/413
[58] Field of Search ............................................. 514/413

[56] References Cited

U.S. PATENT DOCUMENTS 4,089,969  5/1978  Muchowski et al. ................. 514/413
4,454,151  6/1985  Waterbury ............................ 514/413

OTHER PUBLICATIONS

Yu et al, Chemical Abstracts, vol. 109 (1988) 134901x.
Journal Of Clinical Pharmacology, vol. 31, No. 5, May 1991, pp. 401–418, Vasant V. Ranade, "Drug Delivery Systems. 6. Transdermal. Drug Delivery" *pp. 401 and 410*.
Chemical Abstracts, vol. 115, No. 16, 21 Oct. 1991, Columbus, Ohio, US: Abstract No. 166660h, p. 490; *abstract* & JP-A-03 072 433 (Hisamitsu Pharmaceutical Co. Inc.) 28 Apr. 1989.

*Primary Examiner*—Richard L. Raymond
*Attorney, Agent, or Firm*—Bucknam and Archer

[57] ABSTRACT

A fomentation containing ketorolac, one of nonsteroidal anti-inflammatory analgesics, or a salt thereof as the efficacious ingredient, and a base comprising a water-soluble high-molecular substance, a humectant, water and, if necessary, an absorption promoter.

10 Claims, 1 Drawing Sheet

KETOROLAC-CONTAINING FOMENTATION

TECHNICAL FIELD

This application is a 371 of PCT/JP92/01446, filed Nov. 6, 1992.

The present invention relates to a fomentation to be used as an external anti-inflammatory analgesic and, in particular, it relates to a fomentation containing ketorolac (generic name), which is a nonsteroidal anti-inflammatory analgesic or 1.0 a salt thereof, as an efficacious ingredient.

BACKGROUND ART

The compound used as the efficacious or active ingredient in the present invention is generally called ketorolac and the formal chemical name thereof is (±)-5-benzoyl-2,3-dihydro-1H-pyrrolidine- 1-carboxylic acid (or 5-benzoyl-1,2-dihydro -3H-pyrrolo[1,2-a]pyrrole-1-carboxylic acid). Ketorolac was first synthesized by Syntex (U.S.A.) and disclosed as a compound having a remarkable anti-inflammatory analgesic effect in Japanese Patent Gazette No. Sho 62-54109 (54109/1987). Examples of the preparations containing ketorolac or its salt include an internal remedy and an injection disclosed in Japanese Patent Laid-Open Gazette No. Sho 61-191686 (191686/1986), and eye drops for local application described in Japanese Patent Laid-Open Gazette No. Sho 58-172314 ( 172314/1983 ).

Thus, only pharmaceutical preparations such as internal remedies, injections or eye drops each containing ketorolac were disclosed in the prior art, but no plasters containing ketorolac were suggested at all. Therefore, neither description of the fomentation containing ketorolac nor description of its formulation was found at all. Thus it was extremely difficult to anticipate whether ketorolac is usable as the efficacious or active ingredient of a fomentation and an excellent fomentation can be thus developed.

As described above, no attention was directed to the fomentation containing ketorolac as the active ingredient and no investigation was made thereon heretofore. As a matter of course, such a fomentation has not been put into practical use as yet.

Thus the inventors were interested in ketorolac having a remarkable anti-inflammatory analgesic effect in such conventional preparations as above. After their intensive investigations made in an attempt to obtain a fomentation in which ketorolac exhibits a remarkable efficacious effect, the inventors have foundan unexpected fact that ketorolac is difficultly soluble in a fomentation base and is enclosed in the form of crystals therein. The inventors have also found there are raised physical problems of, for example, the compatibility of ketorolac with the base, the stability of the active ingredient, and the reduction in exertion of the medicinal effect due to a decrease in releasability of the active ingredient from the base and percutaneous absorbability of said ingredient. It has been thus found that the development of a desired ketorolac-containing fomentation is difficult unless there are solved problems of the pharmaceutical manufacturing, formulation, design and exertion of the medicinal effect of the desired fomentation.

DISCLOSURE OF THE INVENTION

Therefore, an object of the present invention is to solve the above-described problems and, in particular, it is to provide an optimum anti-inflammatory analgesic ketorolac-containing fomentation by intensively investigating to find a suitable fomentation base comprising a water-soluble high-molecular polymer, a humectant and water, and a suitable formulation of the optimum fomentation; an absorption promoter for promoting the release of the active ingredient from the fomentation and the percutaneous absorption of the released active ingredient; and the base ingredients such as an excipient, an abirritant, a pH regulator, etc.

After their intensive investigations made for the purpose of solving the above-described problems, the inventors have found that an optimum fomentation can be developed by incorporating ketorolac (including a salt thereof; the same shall apply hereinafter) as the active ingredient either into a fomentation base comprising a water-soluble high-molecular polymer, a humectant and water or into the same base further incorporated with an excipient, an abirritant, a pH regulator, etc. as required. The present invention has been completed on the basis of this finding.

There will hereunder be made a detailed description of the ketorolac-containing fomentation of the present invention.

Ketorolac used as the active ingredient in the present invention includes not only pharmaceutically acceptable salts thereof but also ester derivatives and optical isomers thereof. The inorganic salts thereof include sodium, potassium, ammonium, calcium, magnesium and aluminum ones. The organic salts of ketorolac are, for example, primary, secondary and tertiary amines, amino acids and cyclic amines and other amines such as isopropylamine, diethylamine, ethanolamine, tromethamine, lysine, arginine, histidine, piperidine, piperazine, choline and caffeine.

The proportion of ketorolac used as the active ingredient is 0.05 to 10% by weight, preferably 0.1 to 5% by weight and still preferably 0.1 to 3% by weight, based on the whole fomentation. This proportion greatly affects the exertion of the medicinal effect.

The water-soluble high-molecular substances used as a base ingredient are selected from among natural, semisynthetic and synthetic high-molecular substances.

The natural high-molecular substances include, gelatin, hyaluronic acid and salts thereof, collagen, xanthan gum, acacia gum, guar gum, carrageenan, alginic acid, sodium alginate, agar, gum arabic, tragacanth gum, karaya gum, pectin, starch, etc.

The semisynthetic high-molecular substances include methylcellulose, ethylcellulose, hydroxyethylcellulose, sodium carboxymethylcellulose, soluble starch, carboxymethylstarch, dialdehyde starch.

The synthetic high-molecular substances include polyvinyl alcohol, polyvinylpyrrolidone, polyvinyl methacrylate, polyacrylic acid, polysodium acrylate, polyacrylic acid copolymers (such as carboxyvinyl polymer), polyethylene oxide, methyl vinyl ether/maleic anhydride copolymer, and isobutylene/maleic anhydride copolymer. The water-soluble high-molecular substances also include those treated with a known crosslinking agent or a polymerizing agent (polymerization initiator) as a matter of course.

These water-soluble high-molecular substances can be used either singly or in combination of two or more of them according to the formulation. The combinations particularly preferred are gelatin/polyvinyl alcohol gelatin/polysodium acrylate and gelatin/polyvinyl alcohol/polysodium acrylate.

The proportion of the water-soluble high-molecular compound used is 1 to 50% by weight, preferably 3 to 30% by weight and more preferably 5 to 20% by weight, based on the whole fomentation. The above-described formulation comprising the ingredients in the above-described proportions brings about remarkable improvements in the enhancement and persistence of moisture retention, stability, percutaneous (skin) adhesion, releasability of the active ingredient from the base, percutaneous absorbability, the prevention of stickiness and sagging of the base, the relief of pain caused by peeling, and the reduction of remains of the base after peeling.

The humectants used herein include glycerol, propylene glycol, sorbitol, ethylene glycol, diethylene glycol, polyethylene glycol, polypropylene glycol and 1,3-butylene glycol. They are used either singly or jointly.

The proportion of the humectant is 3 to 60% by weight, preferably 5 to 50% by weight and more preferably 10 to 45% by weight, based on the whole fomentation. This proportion brings about improvements in the maintenance of suitable moisture in the fomentation, the persistence of cooling effects therein, the vaporization of water, and the releasability of the active ingredient from the base and the percutaneous absorbability of the ingredient.

The proportion of water indispensable for the fomentation base is 10 to 804 by weight, preferably 20 to 70% by weight and more preferably 25 to 65% by weight, based on the whole fomentation. This proportion brings about improvements in the stability of the fomentation base and the persistence of the cooling effect thereof, as well as in the release of the active ingredient from the base and the percutaneous absorbability of the active ingredient.

By suitably incorporating an absorption promoters into the fomentation of the present invention, the percutaneous absorption of the active ingredient will be promoted or the medicinal effect thereof will last for a long time, whereby the resulting fomentation can be excellent.

The absorption promoters include diisopropyl adipate, polyethylene glycol, lecithin, dimethyl sulfoxide, isopropyl, myristate, squalane, squalene, horse balm, crotamiton, n-octyl-$\beta$-D-glucoside (OG), n-octyl-$\beta$-D-thioglucoside (OTG), azone, 1-[2-(decylthio)ethyl] azacyclopentane-2-one (hereinafter referred to as "HPE-101"), 1-menrhone, 1-menthol, peppermint oil, eucalyptus oil, 1-limonene, d-limonene, dl-limonene and other essential oils; surfactants such as glycerol/fatty acid esters, sorbitan/fatty acid esters, propylene glycol/fatty acid esters, polyoxyethlene (20EO) sorbitan monooleate (trade name: Polysorbate 80), polyoxyethylene (hereinafter referred to as "POE")-hardened castor oil, POE sorbitan monolaurate, POE nonylphenyl ether, POE lauryl ether, POE (40) stearate, POE (20) monostearate, lauric acid diethanolamide, sodium lauryl sulfate, lauromacrogol and polyethylene glycol monostearate; and many other known absorption promoters can be used. These absorption promoters are used either singly or jointly.

The proportion of the absorption promoter is in the range of 0.01 to 10% by weight, preferably 0.1 to 7% by weight and more preferably 0.3 to 5% by weight, based on the whole fomentation. This proportion serves to promote the percutaneous absorption of the fomentation and improve the persistence of the medicinal effect thereof, whereby the resulting fomentation can be a excellent one.

The fomentation of the present invention can further contain, if necessary, an excipient, an abirritant, an adjuvant for drug efficacy, a pH regulator, etc.

Examples of the excipients include fillers such as kaolin, zinc oxide, titanium oxide, talc, bentonite and hydrated aluminum silicate; antiseptics such as thymol, methylparaben, benzalkonium chloride and ethylparaben; antioxidants such as ascorbic acid, stearic esters, disodium edetate, dibutylhydroxy-toluene, butylhydroxyanisole and gallic esters; emulsifying agents such as sorbitan/fatty acid esters, glycerol/fatty acid esters, polyethylene glycol/fatty acid esters, polyoxyethylene sorbitan/fatty acid esters and polyoxyethylene alkyl ethers; ultraviolet absorbers such as phenyl salicylate, glycol salicylate, methyl p-aminobenzoate, 2-hydroxy-4-methoxybenzophenone, 2,2'-dihydroxy-4,4'-dimethoxybenzophenone and 2-hydroxy-4-methoxybenzophenone-5 -sulfonic acid; crosslinking agents and polymerizing agents (or polymerization initiators) such as alkaline earth metal compounds, e.g. calcium chloride, calcium carbonate and magnesium chloride, aluminum compounds, e.g. potash alum, ammonia alum and aluminum hydroxide, aldehydes, e.g. formaldehyde, glyoxal, glutaraldehyde and dialdehyde starch, epoxy compounds, and isocyanate compounds; tackifiers such as polybutene, natural latex, vinyl acetate emulsion and polyacrylic ester emulsion. The excipients can be used either singly or jointly to develop a more excellent fomentation.

To relieve users from the stimulus (irritation) of the skin caused by the fomentation, the following abirritants are used: antihistamines such as diphenhydramine hydrochloride, diphenhydramine tannate, chlorpheniramine dl-maleate, chlorpheniramine d-maleate and chlorpheniramine maleate; antiallergic agents such as amlexanox, ibudilast, azelastine, oxatomide, sodium cromoglicate, tazanolast, terfenadine, tranilast, ketotifen fumarate and repirinast, and steroidal drugs; glycyrrhizic acid, glycyrrhetic acid, $\alpha$-, $\beta 0$ and Y-cyclodextrins; and compounds derived from cyclodextrins. The side effects on the skin can be inhibited by using these compounds in appropriate proportions.

The adjuvants for drug efficacy can be suitably incorporated into the fomentation. They include 1-menthol, camphor, eucalyptus oil, cayenne extract, capsaicine, vitamin E, platonium, scopolia extract, phellodendron bark powder, acesculus extract, belladonna extract, nonylic acid vanillylamide, turpentine oil and benzyl nicotinate. As described above, 1-mentol and eucalyptus oil also function as the absorption promoter.

The pH regulators usable herein include organic acids such as citric, acetic, malic, succinic and tartaric acids; and water-soluble organic amines such as triethanolamine, diisopropanolamine and diethanolamine. The pH of the fomentation is controlled to be in the range of 4 to 8, preferably 4.5 to 7 and more preferably 5 to 6.5 to relieve users from the skin stimulus, to improve the releasability of the active ingredient from the base, the percutaneous absorbability of the active ingredient and the stability of the base, and to maintain the adhesion of the base. The amount of the pH regulator used is suitably selected depending on the desired pH.

There will hereunder be made a description of the process for producing the ketorolac-containing fomentation of the present invention.

First, ketorolac is mixed with an absorption promoter as required, to obtain a homogeneous mixture (A). Then, a water-soluble high-molecular substance is mixed with water and a humectant to obtain a dispersion which is, if necessary, incorporated with an excipient and other additives to obtain a kneaded blend (B). Thereafter, the mixture (A) is added to the blend (B) and kneaded together to obtain a homogeneous kneaded blend. The resulting kneaded blend is spread over a support by an ordinary method and then covered with a releasable coating.

The supports, which may be used here, are a stretchable or unstretchable woven fabric, knit, nonwoven fabric, nonwoven paper and the like. The releasable coatings may be suitably selected from plastic films such as polyethylene, polypropylene and polyester films and from releasable papers.

The order in which the above preparations, efficacious ingredients and other ingredients are incorporated in the above-described production process is only an example, and the process for producing the fomentation of the present invention is not limited to such an order as above.

BEST MODE FOR CARRYING OUT THE INVENTION

Figure 1:
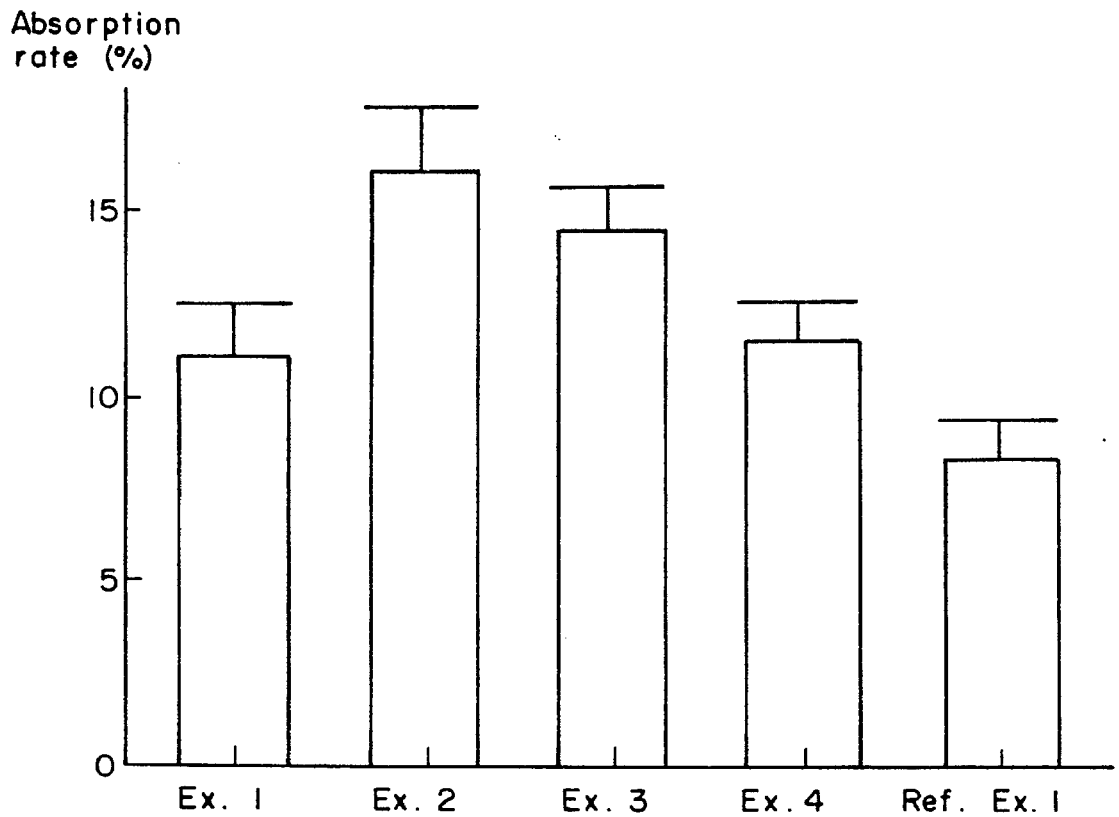
FIG. 1 is a graph showing the percutaneous absorption rates of ketorolac by human beings.

The following Referential Example and Examples will further illustrate the preparation of the fomentation of the present invention, which Examples by no means limit the invention. In the following Referential Example and Examples, parts are given by weight.

Referential Example 1

44.7 parts of purified water, 6 parts of gelatin, 3.5 parts of polyvinyl alcohol and 5 parts of kaolin were fed into a mixer and dissolved (or melted) therein at 50° C. to obtain a homogeneous dispersion. A dispersion comprising 25 parts of glycerol and 3 parts of polysodium acrylate as well as a solution of 2.5 parts of polyacrylic acid in 10 parts of purified water, each of which had been prepared in advance, was thrown into said homogeneous dispersion and stirred together to obtain a homogeneous kneaded blend. Then, 0.3 parts of ketoprofen were mixed with said blend to obtain a homogeneous kneaded blend.

This resultant kneaded blend was coated on a given nonwoven fabric in a coating weight of 10 g/140 cm$^2$ with a spreader, covered with a polypropylene film and then cut into a predetermined size to obtain intended products.

Example 1

44.7 parts of purified water, 6 parts of gelatin, 3.5 parts of polyvinyl alcohol and 5 parts of kaolin were fed into a mixer and dissolved (or melted) therein at about 50° C. to obtain a homogeneous dispersion. A dispersion comprising 25 parts of glycerol and 3 parts of polysodium acrylate as well as a solution of 2.5 parts of polyacrylic acid in 10 parts of purified water, each of which dispersion and solution had been prepared in advance, was thrown into said homogeneous dispersion, stirred together to obtain a homogeneous kneaded blend. 0.3 parts of ketorolac were mixed with said blend to obtain a homogeneous kneaded blend.

This resultant kneaded blend was applied to a given nonwoven fabric to a depth expressed as 10 g/140 cm$^2$ with a spreader, covered with a polypropylene film and then cut into a predetermined size to obtain intended products.

Example 2

43.7 parts of purified water, 6 parts of gelatin, 3.5 parts of polyvinyl alcohol and 5 parts of kaolin were fed into a mixer and dissolved therein at about 50° C. to obtain a homogeneous dispersion. A dispersion comprising 25 parts of glycerol and 3 parts of polysodium acrylate as well as a solution of 2.5 parts of polyacrylic acid in 10 parts of purified water, each of which had been prepared in advance, was thrown into said homogeneous dispersion and the resultant mixture was stirred to obtain a homogeneous kneaded blend. 0.3 parts of ketorolac and 1 part of crotamiton were mixed with said kneaded blend to obtain a homogeneous blend.

This resultant kneaded blend was applied to a given nonwoven fabric in a coating thickness expressed as 10 g/140 cm$^2$ with a spreader, covered with a polypropylene film and then cut into a predetermined size to obtain intended kneaded products.

Example 3

43.7 parts of purified water, 6 parts of gelatin, 3.5 parts of polyvinyl alcohol and 5 parts of kaolin were fed into a mixer and dissolved therein at about 50° C. to obtain a homogeneous dispersion. A dispersion comprising 25 parts of glycerol and 3 parts of polysodium acrylate as well as a solution of 2.5 parts of polyacrylic acid in 10 parts of purified water, each of which had been prepared in advance, was thrown into said homogeneous dispersion and the resultant mixture was stirred to obtain a homogeneous kneaded blend. 0.3 parts of ketorolac tromethamine and 1 part of peppermint oil were mixed with said kneaded blend to obtain a homogeneous kneaded blend.

This resultant kneaded blend was applied to a given nonwoven fabric in a coating thickness expressed as 10 g/140 cm$^2$ with a spreader, covered with a polypropylene film and then cut into a predetermined size to obtain intended products.

Example 4

44.7 parts of purified water, 6 parts of gelatin, 3.5 parts of polyvinyl alcohol and 5 parts of kaolin were fed into a mixer and dissolved therein at about 50° C. to obtain a homogeneous dispersion. Not only a dispersion comprising 25 parts of glycerol and 3 parts of polysodium acrylate but also a solution of 2.5 parts of polyacrylic acid in 10 parts of purified water, each of which had been prepared in advance, was thrown into said homogeneous dispersion and the resultant mixture was stirred to obtain a homogeneous kneaded blend. 0.3 parts of ketorolac tromethamine were mixed with said kneaded blend to obtain a homogeneous kneaded blend.

This resultant kneaded blend was applied to a given nonwoven fabric to a depth expressed as 10 g/140 cm$^2$ with a spreader, covered with a polypropylene film and then cut into a predetermined size to obtain intended products.

Examples 5 to 17

Homogeneous blends respectively comprising the components in the proportions specified in Table 1 were obtained in the same manner as in Examples 1 to 4.

The resultant blends were each applied to a given nonwoven fabric in a coating thickness expressed as 10 g/140 cm$^2$ with a spreader, covered with a polypropylene film and then cut into a predetermined size to obtain intended products.

TABLE 1

| Base | Ex. 5 | 6 | 7 | 8 | 9 | 10 | 11 | 12 | 13 | 14 | 15 | 16 | 17 |
|---|---|---|---|---|---|---|---|---|---|---|---|---|---|
| Ketorolac | 0.3 | 0.3 | 0.1 | 0.5 | 1.0 | 2.0 | | | | | | | |
| Ketorolac tromethamine | | | | | | | 0.1 | 0.3 | 0.3 | 0.5 | 1.0 | 2.0 | 5.0 |
| Gelatin | 6 | | 5 | 5 | 8 | 5 | 5 | 2 | 5 | 6 | 5 | 7 | 5 |
| Polyvinyl alcohol | | | 2.5 | 2.5 | 2.5 | 2.5 | 2.5 | 2.5 | 3.5 | 3.5 | 3.5 | 2.5 | 2.5 |
| Polysodium acrylate | 3 | 6 | 3 | 3 | 2 | | 3 | 3 | 2 | 3 | 3 | 3 | 3 |
| Polyvinyl-pyrrolidone | | | | 1 | | | | | | | | | |
| Sodium carboxymethyl-cellulose | | | | 2 | | | | | | | | | |
| Carboxyvinyl polymer (Carbopol) | | | | | | 1 | | | | | | | |
| Methyl vinyl ether/maleic anhydride copolymer | | 1 | | | | | | 2 | | | | | |
| Polyacrylic acid | 2.5 | 4 | 2 | | 2 | 2 | | 2 | 3 | | 2 | | 2 |
| Glycerol | 25 | 30 | 25 | 25 | 40 | 25 | 20 | 20 | 30 | 10 | 25 | 25 | 10 |
| Propylene glycol | | | | | | | | | | 10 | | | |
| Sorbitol | | | | 10 | | | 7 | | | | | | |
| Ethylene glycol | | | | | | | | | 15 | | | | |
| 1, 3-Butylene glycol | | | | | | | | 10 | | | | | |
| Water | 57.2 | 54.2 | 55.4 | 46 | 37.5 | 55.5 | 56.4 | 56.1 | 36.7 | 62.9 | 52.9 | 52.5 | 67.4 |
| Crotamiton | | | | | | 1 | | | | 1 | | | |
| Polyethylene glycol monostearate | | | | | | | | | | | 0.5 | | |
| Peppermint oil | | | 1 | | | 1 | | | | | | | |
| Oleic acid | | | | 1 | | | | | | | | | |
| Glycol salicylate | | | | | | | | 1 | | | | | |
| Eucalyptus oil | | | | | | | | | | 1.5 | | | |
| d-Limonene | | | | | 1 | | | | | | | | |
| Polysorbate 80 (trade name) | | | | | | | | | | | | 1 | |
| Diisopropyl adipate | | | | | | | | | | | | | 1 |
| Isopropyl myristate | 1 | | | | | | | | | | | | |
| 1-Menthol | | 0.5 | | | | | | | | | | | |
| Azone | | | | | | | | 1 | | | | | |
| HPE-101 | | | | | | | | | | | | | 1 |
| Triethanolamine | | | | | | | | | | 0.1 | | | |
| Diisopropanolamine | | | | | | | | | | | 0.1 | | |
| Diphenhydramine hydrochloride | | | | | | | | | | | | | 0.1 |
| Glycyrrhizic acid | | | | | | | | 0.1 | | | | | |
| Excipient | 5 | 5 | 5 | 5 | 5 | 5 | 3 | 3 | 3 | 3 | 7 | 7 | 3 |
| In total | 100 | 100 | 100 | 100 | 100 | 100 | 100 | 100 | 100 | 100 | 100 | 100 | 100 |

The following Tests will further illustrate the specific effects of the present invention.

Test 1 Pain-killing test on rats (Experimental method)

Randall and Selitto method

Groups each consisting of Wistar-strain rats weighing around 150 g were used. Each of the test fomentations (5×4 cm) prepared as the intended products in Examples 1 to 4 was applied to the right hind leg of the rat and then removed therefrom 4 hours later. Immediately thereafter, a yeast solution (20%, 0.1 ml) as an inflammation-causing agent was applied by hypodermic injection to the sole of the hind leg to which the fomentation had been applied. Three hours after, a pain threshold value was determined. The medicinal effect was given in terms of an increase rate with respect to the threshold value of the control group.

(Experiment results)

The external analgesic effect of each test fomentation on lowering the pain threshold value three hours after the application of the yeast was examined. The results are given in Table 2. As compared with the control, test fomentations B, C and D respectively exhibited remarkable analgesic effects and, in particular, respectively exhibited increases of the pain threshold value by 72.54, 72.54 and 60.0%. A considerable analgesic effect of even the test fomentation A was also recognized to increase the pain threshold value by 41.04.

TABLE 2

| Test fomentation | Threshold value elevation rate (%) |
|---|---|
| A (Example 1) | 41.0 |
| B (Example 2) | 72.5 |
| C (Example 3) | 72.5 |
| D (Example 4) | 60.0 |

Test 2 Percutaneous absorption test on human beings

Each of the test fomentations obtained by stamping the intended products prepared in Examples 1 to 4 and Referential Example 1 into pieces each having a size of 3×3 cm², and the piece was applied to the upper part of the back of each of 6 healthy volunteers and then recovered 16 hours later to determine the amount of remains of the ketorolac by HPLC.

Quantiative determination method

The recovered fomentation was treated to extract the remaining medicinal ingredient with 70 ml of methanol under reflux for 2 hours. After the completion of the extraction, the methanol used was increased in amount to 100 ml by adding fresh methanol thereto, thereby obtaining a sample for HPLC.

HPLC conditions mobile phase: 0.2% acetic acid/water: acetonitrile (55:45), absorption wavelength: 254 nm, column: TSK gel ODS-80TM, flow rate: 1.0 ml/min.

Absorption rate of human being (1-amount of remains/initial content)×100. (The absorption rate of human being was calculated by the above formula). The results are shown in FIG. 1.

Test 3 Test of penetration through the skin of hairless mouse

Hairless mice were skinned. The skin was fixed in a device in such a manner that the corneous layer made the donor phase and the corium made the receptor phase. The test fomentations each having a diameter of 1 cm prepared by stamping the intended products obtained in Examples 1 to 4 and Referential Example 1 were each applied to the corneous layer side of the skin.

A phosphate buffer solution having a pH of 7.4, as the receptor solution, was fed into the receptor phase.

After, 4, 8, 12 and 24 hours, the receptor solution was sampled and the amount of the penetrated medicine was determined by HPLC, and the skin penetration rate was calculated according to the following formula:

skin penetration rate =(amount of medicine penetrated through the skin)/(initial amount of medicine)×100

HPLC conditions mobile phase: 0.2% acetic acid/water: acetonitrile (55:45), absorption wavelength: 254 nm, column: TSK gel ODS-80TM, flow rate: 1.0 ml/min.

The intended products obtained in Examples 1 to 4 of the present invention exhibited the skin penetration rates higher than that of the sample obtained in Referential Example 1 to prove the effect of the present invention.

Figure 2:
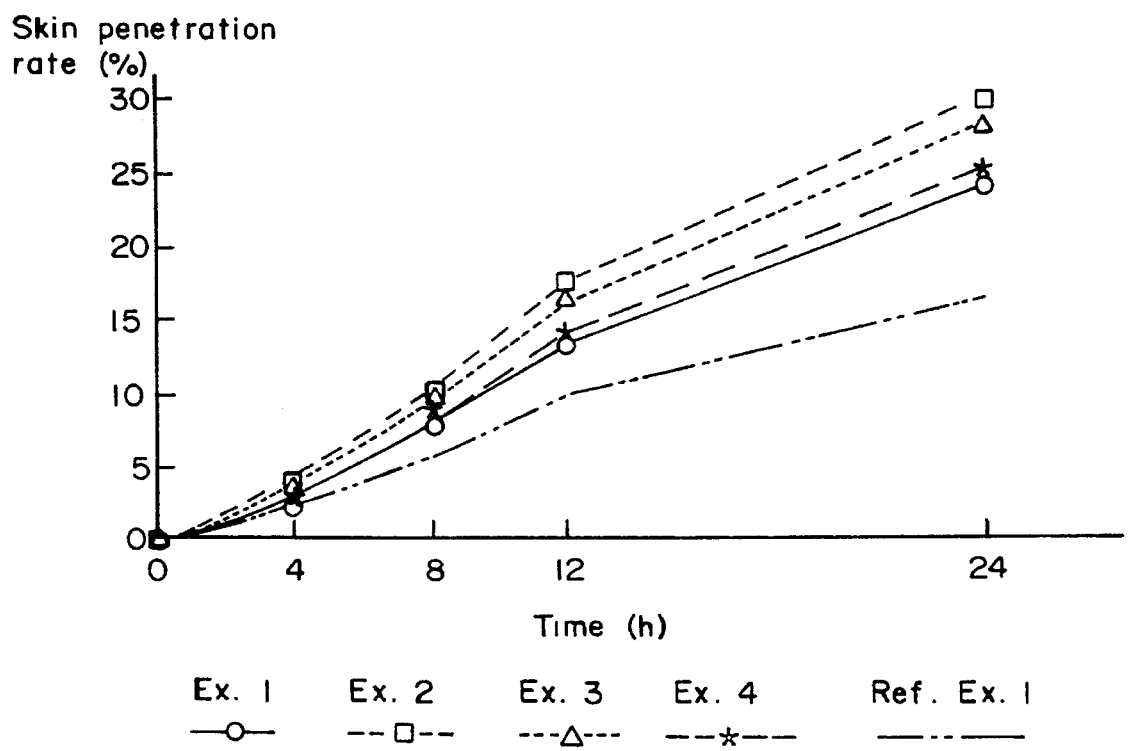
FIG. 2 is a graph showing the rates of penetration of ketorolac through the skin of hairless mice.

The results are shown in FIG. 2.

Industrial Applicability

The fomentation of the present invention has the following excellent characteristics:

a) excellent release of the medicine from the base, b) high adhesion to the skin for percutaneous administration, c) only slight skin stimulus, d) excellent shape retention of the plaster per se, without sagging, softening and stickiness, e) excellent percutaneous absorption, f) excellent feeling of coolness due to excellent moisture retention and persistent cooling effect, g) remarkable anti-inflammatory analgesic activity, and h) excellent persistence of the medicinal efficacy and excellent long-lasting effect.

Since the fomentation of the present invention has thus excellent functions and effects, it follows that an excellent anti-inflammatory analgesic fomentation for external use can be provided. The fomentation is a medicinal preparation useful for the treatment of rheumatoid arthritis, arthrosis deformans, lumbago, scapulohumeral periarthritis, contusion, sprain, fracture, carcinomatous pain, myalgia, paratendinitis, tendinous tendovaginitis, humeral epicondylitis, posttraumatic swelling and pain, and gout.

We claim:

1. A fomentation which consists of 1 to 50% by weight of at least one water-soluble high-molecular substance, 3 to 60% by weight of at least one humectant, 10 to 80% by weight of water, 0.05 to 10% by weight of ketorolac or a salt thereof, at least one excipient, a pH regulator to keep the pH at 4.5–7, an abirrant and at least one adjuvant of drug efficacy.

2. The fomentation according to claim 1, wherein said high molecular weight water soluble substance is a member selected from the group consisting of polyvinyl alcohol, polysodium acrylate and polyacrylic acid, said humectant is a member selected from the group consisting of glycerol, propylene glycol, sorbitol, 1,2-butylene glycol, said adjuvant of drug efficacy is l-menthol or eucalyptus oil and the abirritant is diphenydramine hydrochloride or glycyrrhetic acid.

3. The fomentation according to claim 2, wherein based on the weight of said fomentation, said water soluble high molecular weight substance is in the amount of 5–20%, said humectant is in the amount of 10–45%. and water is in the amount of 25–65% by weight.

4. The combination of a fomentation according to claim 1 and a non-woven fabric, said fomentation being spread on said non-woven fabric to a depth of 10 g/140 cm².

5. A fomentation which consists of 1 to 50% by weight of at least one water-soluble high-molecular substance, 3 to 60% by weight of at least one humectant, 10 to 80% by weight of water, 0.05 to 10% by weight of ketorolac or a salt thereof, at least one absorption promoter, at least one excipient, a pH regulator to keep the pH at 4.5–7, an abirrant and at least one adjuvant for drug efficacy.

6. The fomentation according to claim 5, wherein said high molecular weight water soluble substance is a member selected from the group consisting of gelatin, polyvinyl alcohol, polysodium acrylate and polyacrylic acid, said humectant is a member selected from the group consisting of glycerol, propylene glycol, sorbitol, and 1,3-butylene glycol, said adjuvant is l-menthol or eucalyptus oil, the abirritant is diphenhydramine hydrochloride or glycyrrhetic acid and the absorption promoter is a member selected from the group consisting of polyethylene glycol, crotamiton, peppermint oil and limonene.

7. The fomentation according to claim 5 which consists based on the weight of said fomentation, of 0.1–3% of ketorolac, 5–20% of said water soluble high molecular weight substance, 10–45% of said humectant, 25–65% of water, 0.3–5% of said absorption promoter by weight.

8. The combination of a fomentation according to claim 5 and a non-woven fabric, said fomentation being spread on said non-woven fabric to a depth of 10 g/140 cm$^2$.

9. The combination according to claim 4 which additionally comprises a releasable coating applied over said non-woven fabric, said coating being a member selected from the group of polyethylene, polypropylene and polyester fibers.

10. The combination according to claim 8 which additionally comprises a releasable coating applied over said non-woven fabric, said coating being a member selected from the group of polyethylene, polypropylene and polyester fibers.

* * * * *